US011155612B2

(12) United States Patent
Licea Navarro et al.

(10) Patent No.: US 11,155,612 B2
(45) Date of Patent: Oct. 26, 2021

(54) VNAR ANTIBODY WHICH BINDS VEGF FOR USE IN DOGS OR CATS

(71) Applicants: CENTRO DE INVESTIGACIÓN CIENTÍFICA Y DE EDUCACIÓN SUPERIOR DE ENSENADA, BAJA CALIFORNIA, Ensenada Baja California (MX); LABORATORIOS SILANES, S.A. DE C.V., Mexico City (MX); TERACLÓN IDF, Madrid (ES); NOVA PROTEINS S.A. DE C.V., Ensenada Baja California (MX)

(72) Inventors: Alexei Fedorovish Licea Navarro, Ensenada (MX); Dalia Vanessa Millán Gómez, Ensenada (MX); Liliana Noemi Sánchez Campos, Ensenada (MX); Carolina Elosua Portugal, Madrid (ES); Jorge Fernando Paniagua Solís, Madrid (ES); Salvador Dueñas Espinoza, Ensenada (MX)

(73) Assignee: CENTRO DE INVESTIGACIÓN CIENTÍFICA Y DE EDUCACIÓN SUPERIOR DE ENSENADA, BAJA CALIFORNIA

( * ) Notice: Subject to any disclaimer, the term of this patent is extended or adjusted under 35 U.S.C. 154(b) by 0 days.

(21) Appl. No.: 16/606,908

(22) PCT Filed: Apr. 20, 2018

(86) PCT No.: PCT/MX2018/050010
§ 371 (c)(1),
(2) Date: Oct. 21, 2019

(87) PCT Pub. No.: WO2018/194441
PCT Pub. Date: Oct. 25, 2018

(65) Prior Publication Data
US 2020/0165331 A1 May 28, 2020

Related U.S. Application Data

(60) Provisional application No. 62/488,634, filed on Apr. 21, 2017.

(51) Int. Cl.
C07K 16/22 (2006.01)
A61P 35/00 (2006.01)

(52) U.S. Cl.
CPC .............. C07K 16/22 (2013.01); A61P 35/00 (2018.01)

(58) Field of Classification Search
None
See application file for complete search history.

(56) References Cited

U.S. PATENT DOCUMENTS

| 8,496,933 B2 | 7/2013 | Paniagua-Solis et al. |
| 8,865,431 B2 | 10/2014 | Dooley et al. |
| 9,399,677 B2 | 7/2016 | Paniagua-Solis et al. |
| 10,370,442 B2 | 8/2019 | Portugal et al. |

FOREIGN PATENT DOCUMENTS

| EP | 3133085 A1 | 2/2017 |
| WO | 2005118629 A1 | 12/2005 |

OTHER PUBLICATIONS

Camacho-Villegas et al. Mar. Drugs 16: 113, 2018 (13 pages).*
Steven et al. Front. Immunol., vol. 8, article 1361, 2017 (15 pages).*
Adelfinger, Marion, et al., Evaluation of a New Recombinant Oncolytic Vaccinia Virus Strain GLV-5b451 for Feline Mammary Carcinoma Therapy; PLOS One, www.plosone.org; Aug. 2014, vol. 9, Issue 8, e104377.
Marina Kovaleva, Laura Ferguson, John Steven, Andrew Porter & Caroline Barelle (Aug. 4, 2014) Shark variable new antigen receptor biologics—a novel technology platform for therapeutic drug development, Expert Opinion on Biological Therapy, 14:10, 1527-1539, DOI: 10.1517/14712598.2014.937701.
Michishita, Masaki, et al., "Antitumor Effect of Bevacizumab in a Xenograft Model of Canine Hemangiopericytoma", J Pharmacol Sci 121, 339-342 (Jan. 27, 2013).
Navarro, Dr. Alexei Fedorovish Licea, et al., "Tesis defendida por David Rosendo Navarro Apanco y aprobada por el siguiente comité", Centro De Investigación Científica y De Educación Superior De Ensenada (Dec. 10, 2012), English Abstract p. 3.
Patil SS, Gentschev I, Adelfinger M, Donat U, Hess M, et al. (Oct. 16, 2012) "Virotherapy of Canine Tumors with Oncolytic Vaccinia Virus GLV-1h109 Expressing an Anti-VEGF Single-Chain Antibody." PLoS One 7(10): e47472. doi:10.1371/journal.pone.0047472.
Ferrara, N. 2009. VEGF-A: A Critical Regulator of Blood Vessel Growth. European Cytokine network 20(4):158-163.
Saunders (Elsevier), ed. (2009); Ch3-Tissue Renewal, Regeneration and Repair. Robbins and Cotran Pathologic Basis of Disease 8 ed.
Holmes K, Roberts OL, Thomas AM, Cross MJ., Cellular Signaling 19 (2007) 2003-2012. Received Apr. 25, 2007; Accepted May 8, 2007; Available Online Jun. 12, 2007.
Sanchez Socarras, V. 2001, Papel de la Angiogenesis en el Crecimiento Tumoral, Revista Cubana Investigaciones Biomedicas 20(3): 2223-230.
Amoh Y, Yang M, Li L.,Reynoso J, Bouvet M. Moossa AR, Katsuoka K, Hoffman RM, "Nestin-driven Green Fluorescent Protein Transgenic Nude Mouse for Imaging Human Tumor Angiogenesis." Cancer Res. 2005; 65: 5352-5357.

* cited by examiner

Primary Examiner — Christine J Saoud
(74) Attorney, Agent, or Firm — Emerson, Thomson & Bennett, LLC; Roger D. Emerson; Peter R. Detorre

(57) ABSTRACT

The present invention relates to a novel vNAR protein of SEQ ID NO:1 capable of inhibiting the activity of VEGF in carnivorous mammals of the *Canis* and *Felis* genera, thereby inhibiting solid tumors growth of both genres.

Figure 1:
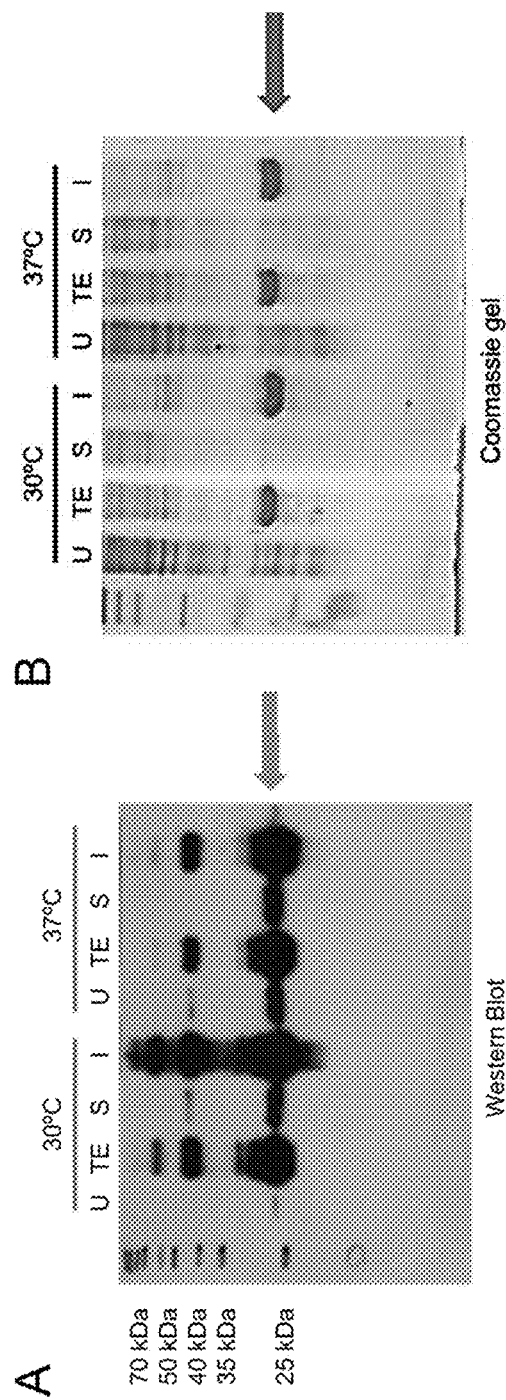

2 Claims, 7 Drawing Sheets
Specification includes a Sequence Listing.

VNAR ANTIBODY WHICH BINDS VEGF FOR USE IN DOGS OR CATS

The vNAR protein sequence of the present invention is identified in the sequence listing as SEQ ID NO:1. The Specification further references the murine VEGF protein sequence identified as SEQ ID NO:2, the cat VEGF protein sequence, identified as SEQ ID NO:3 and the dog VEGF protein sequence, identified as SEQ ID NO:4. These sequences are presented below and provided in the ASCII text file entitled, "SequenceListingUS2019P1032CICESE.txt", created on Feb. 19, 2021 and having a file size 4115 bytes which is hereby incorporated by reference in its entirety.

FIELD OF THE INVENTION

The present invention relates to a novel vNAR protein for the control of neoplastic pathologies. More particularly to a vNAR protein with anti-angiogenic activity, which can be used in the drug manufacturing for the control and/or eradication of solid tumors in companion animals like dogs or cats.

BACKGROUND OF THE INVENTION

The variable domain of the new receptors of antigens or vNAR are attractive structures, based on their size, solubility, thermal stability, and refolding after denaturation. vNARs have a high-variability CDR3, which acquires an extended hairpin shape, that allows insertion into cryptic epitopes. These proteins have been widely used in recent years as options for conventional therapies against infectious diseases such as tuberculosis or induction agents for the production of antisera. One of the options that is currently being studied further is the use of vNARs as therapeutic agents against neoplastic pathologies, due to their small size and high affinity, they present a better biodistribution being able to reach their molecular target in a faster way, crossing easily any of the body barriers. While it is true that attempts have been made to use vNARs as disease control molecules or as detection markers, this approach has always been made to find therapies for human beings, so until now the full potential of vNARs for use in therapies of species not closely related to man has not been explored. In the case of companion animals, dogs and cats are two of the species that would benefit significantly from the use of immunotherapies for the control and/or eradication of pathologies based on the active use of vNARs proteins, since so far, the therapies focused on use drugs designed for humans, so these drugs did not always have the desired effect on these animal species.

Particularly, the case of dogs is of great interest, because in recent years, the search for variants or breeds of dogs has brought impoverishment in the genetic diversity of dogs, mostly caused by the selective cross-linking of close relatives to maintain certain desired morphological characteristics present in the offspring. This cross-linking greatly favors the appearance of degenerative pathologies, most of which are malignant neoplastic growths or solid tumors, which according to the National Cancer Institute of the USA (NCI), are abnormal masses of tissue that, usually do not contain areas with cysts or liquids. Solid tumors can be benign (non-cancerous) or malignant (cancerous). The type of cells that conform them, names the different types of solid tumors. Sarcomas, carcinomas, and lymphomas are examples of solid tumors. Leukemias (blood cancer) usually do not form solid tumors. These growths, better known as cancers, have become a severe problem in certain dog breeds such as boxers, golden retriever, labrador retriever, bulldogs, mastiffs, Saint Bernard, and the bulldog to mention some of the dog breeds most prone to cancer. The treatments currently available to treat cancer in dogs and cats are surgery, chemotherapy, radiotherapy, and immunotherapy. However, immunotherapy is still little used, because most of the commercially available antibodies are designed to target hominid molecular targets, so their success is relatively little in comparison with other types of therapies. Although, chemotherapy has proven to be the best treatment option so far, this entails multiple disadvantages, among which, the high toxicity of the chemical compounds used stands out, because both dogs and cats have liver systems that behave very differently from humans and, therefore, therapies that prove to be effective in humans, are generally very toxic to carnivores. Therefore, the use of vNAR proteins turns out to be one of the most promising ways to be followed to find better control therapies and/or eradication of tumors in dogs and cats.

The majority of tumors present in the animal genera mentioned above are strongly linked to overexpression of endothelial growth factor (VEGF). VEGF is a signaling protein involved in vasculogenesis (de novo formation of the embryonic circulatory system) and angiogenesis (growth of blood vessels from preexisting vessels) (Ferrara, N. 2009. VEGF-A: a critical regulator of blood vessel growth. European Cytokine Network 20(4):158-163). As its name indicate, the actions of VEGF have been studied in vascular endothelial cells, although it also has effects on other cell types (for example, it stimulates the migration of monocytes/macrophages, neurons, renal epithelial cells, and tumor cells) in vitro, VEGF has shown to stimulate the division and migration of endothelial cells. VEGF is also a vasodilator and increases vascular permeability; originally received the name of vascular permeability factor. VEGF is a potent inducer of blood vessel formation during embryonic development (vasculogenesis) and has a fundamental role in the growth of new vessels in adults (angiogenesis) (Saunders (Elsevier), ed. (2009); Ch3-Tissue Renewal, Regeneration and Repair. Robbins and Cotran Pathologic Basis of Disease 8ed). VEGF promotes angiogenesis in the processes of chronic inflammation, scarring, and tumors. VEGF is secreted by many mesenchymal and stromal cells, induces migration of endothelial precursor cells from the bone marrow, and stimulates the proliferation and differentiation of these cells at the angiogenesis sites. When angiogenesis originates from preexisting vessels (and not from precursor cells), VEGF stimulates the survival of endothelial cells, their proliferation, and their motility, initiating the gemmation of new capillaries. The members of the VEGF family perform their function in the target cells through three receptors with intrinsic tyrosine kinase activity: VEGFR-1, VEGFR-2, and VEGFR-3, located in endothelial cells and other cell types. The most important in angiogenesis is VEGFR-2. Ligand-receptor binding causes dimerization of the receptor and its activation by transphosphorylation, although in different places, moments, and intensity. VEGF receptors have an extracellular portion consisting of 7 immunoglobulin-like domains, a single transmembrane region, and an intracellular region containing a cleavage tyrosine kinase domain. VEGF-A joins VEGFR-1 (Flt-1) and VEGFR-2 (KDR/Flk-1). VEGFR-2 seems to mediate almost all known VEGF cellular responses (Olmes K, Roberts O L, Thomas A M, Cross M J. (October 2007). Vascular endothelial growth factor receptor-2: structure, function, intracellular signaling and therapeutic inhibition. Cell Signal 19 (10): 2003-2012). The function of VEGFR-1 is less known, but it is thought to modulate the function of VEGFR-2. In addition, VEGFR-1 could sequester VEGF to prevent its binding with VEGFR-2 (this seems to be especially important during vasculogenesis in the embryo). VEGF-C and VEGF-D, but not VEGF-A, are ligands of the third receptor (VEGFR-3), which mediates lymphangiogenesis. VEGF production can be induced in cells that are not receiving enough oxygen. When a cell is deficient in oxygen, it produces HIF (due to hypoxia-inducible factor), a transcription factor. HIF stimulates the release of VEGF, among other functions (such as erythropoiesis modulation). Circulating VEGF binds to VEGF receptors on endothelial cells, thus triggering a tyrosine kinase pathway that leads to angiogenesis. HIF1 alpha and HIF1 beta are produced continuously, but HIF1 alpha is highly labile in the presence of 02, so it degrades in aerobic conditions. When the cell is under hypoxic conditions, HIF1 alpha persists, and the HIF1alpha/beta complex stimulates the release of VEGF. Establishing a blood vessel system is a central step during embryogenesis. Vascularity (or vascularization) is functioning before the other organs, and from this point, the differentiation and proliferation of endothelial cells must be rigorously controlled by the different cytokines involved in the angiogenesis process to avoid pathological processes. (Sanchez Socarras, V. 2001, Papel de la angiogenesis en el crecimiento tumoral, Revista Cubana Investigaciones Biomédicas 20(3):223-230). Angiogenesis is critical in the early development of cancer and its metastatic spread. There are 2 monoclonal antibodies on the market against VEGF, only 1 of which is used to treat cancer. VEGF neutralizing antibodies have proven to be a very useful tool in the development of new therapies against diseases in which VEGF is actively involved, such as the case of Bevacizumab (Avastin), which is a murine-humanized monoclonal antibody that targets VEGF-A, which is an essential cytokine in the development of angiogenesis. This antibody is used for the treatment of metastatic colorectal cancer.

However, the use of monoclonal antibodies as therapy may have side effects such as immunotoxicity. Therefore, the use of vNARs can greatly overcome the adverse effects associated with immunotherapy in carnivorous animals, because these protein molecules have a very low immunotoxicity in mammals, to which the fact that they are up to ten times smaller compared to other conventional antibodies such as those of human origin.

There are three classes of vNAR, which concentrate their diversity on their CDR (CDR1 and CDR3), which allows them to recognize a wide variety of antigens. The CDR3 of the vNARs is longer compared to the CDR3 of the Ig of humans and mice, which gives it a superior reach towards antigenic sites generally not accessible by other conventional antibodies.

It is known that, by constructing cDNA libraries from the shark antibody repertoire, that is, unimmunized libraries, clones expressing vNAR with a specific binding by a single molecular target can be obtained; being these libraries valuable sources of agents with high affinity. The above, combined with its reduced size, large size of its CDR3, its great stability against external agents, and high resistance to temperature changes makes them suitable as immunotherapy agents.

Given the above, there is a need to provide a new vNAR protein, capable of actively and selectively inhibiting the VEGF of carnivorous mammals; more specifically the VEGF of dogs or cats in order to control and/or eradicate the neoplastic pathologies associated with a high neovascularization of the affected tissues.

SUMMARY OF THE INVENTION

In order to provide a new therapeutic option to treat neoplastic pathologies in carnivorous mammals, particularly those that serve as companion animals, such as dogs or cats, the present invention aims to provide a vNAR protein with the ability to bind specifically to the endothelial vascular growth factor (VEGF) of carnivorous mammals.

Another objective of the present invention is to provide a vNAR protein capable of inhibiting angiogenesis in solid tumors of companion animals.

A further objective of the present invention is to provide a veterinary drug for the supportive treatment of neoplasms, which has as an active ingredient a vNAR protein.

A further objective of the present invention is to provide a supportive treatment method for the control and/or eradication of solid tumors in carnivorous mammals that use a vNAR protein capable of selectively blocking VEGF activity.

The aforementioned objectives, as well as others and the advantages of the present invention, will become apparent from the following detailed description thereof.

DESCRIPTION OF THE INVENTION FIGURES

FIG. 1 shows the expression of anti-VEGF vNAR. The lanes correspond in each case to the total extract without induction (U), total extract after induction time (TE), soluble fraction after cell lysis (S) and insoluble fraction after lysis (I). Equivalent amounts of cell extract were loaded onto the gels. (A) Western blot and chemiluminescence. (B) Coomassie-stained gel.

Figure 2:
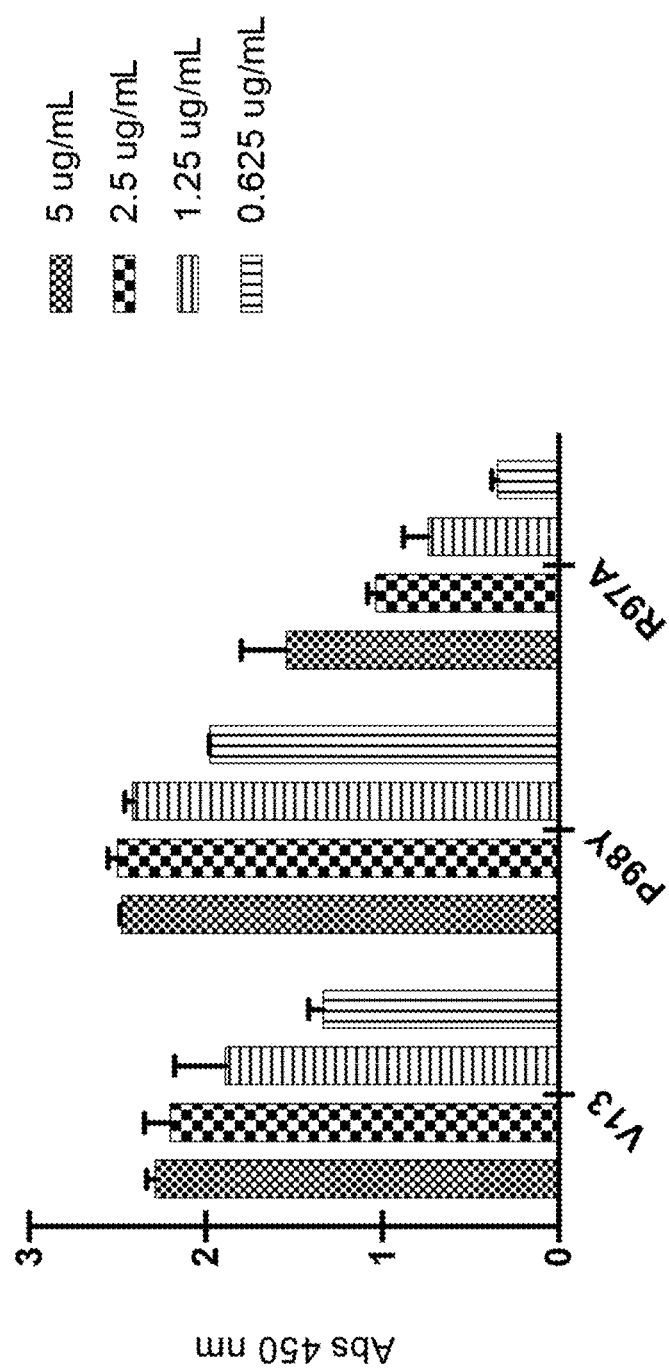

FIG. 2 shows the ELISA titration of two of the generated vNARs (P98Y and R97A). Decreasing concentrations of each vNAR were added to measure the recognition of VEGF compared to V13, which is the parental antibody.

Figure 3:
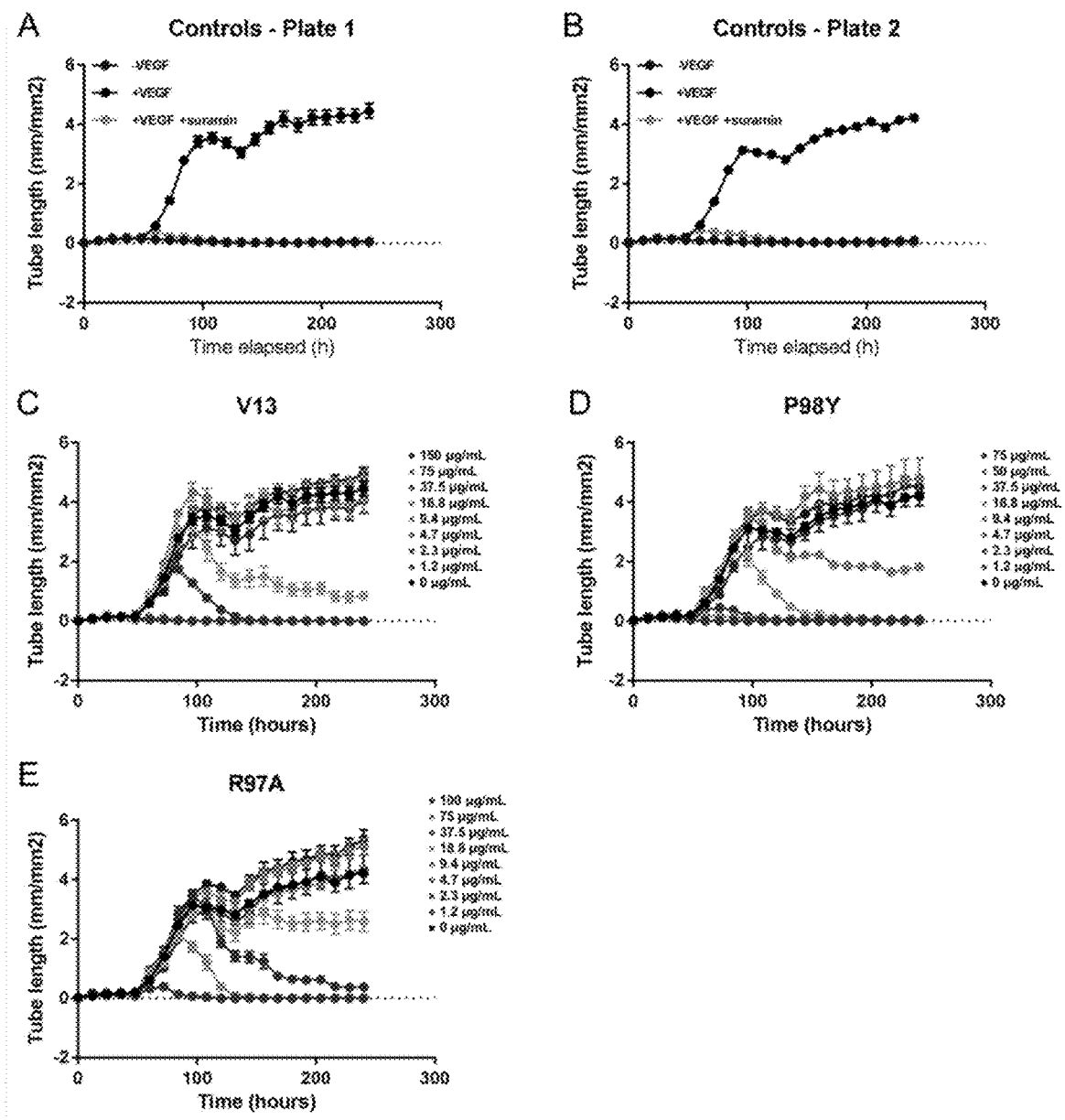

FIG. 3 shows the effects of mutants and parental vNAR (V13) on the length of the newly formed tube. (A and B) forty-eight hours after seeding: untreated cells (−VEGF); treatment with 4 ng/ml of VEGF (+VEGF) and; treatment with 4 ng/ml of VEGF and 100 µM of suramin (+VEGF+suramin).

The length of the tube was quantified for 240 hours, data expressed as the mean of 8 wells±SEM. (C-E) forty-eight hours after seeding, cells treated with 4 ng/ml of VEGF and the indicated concentration of the test compound.

Figure 4:
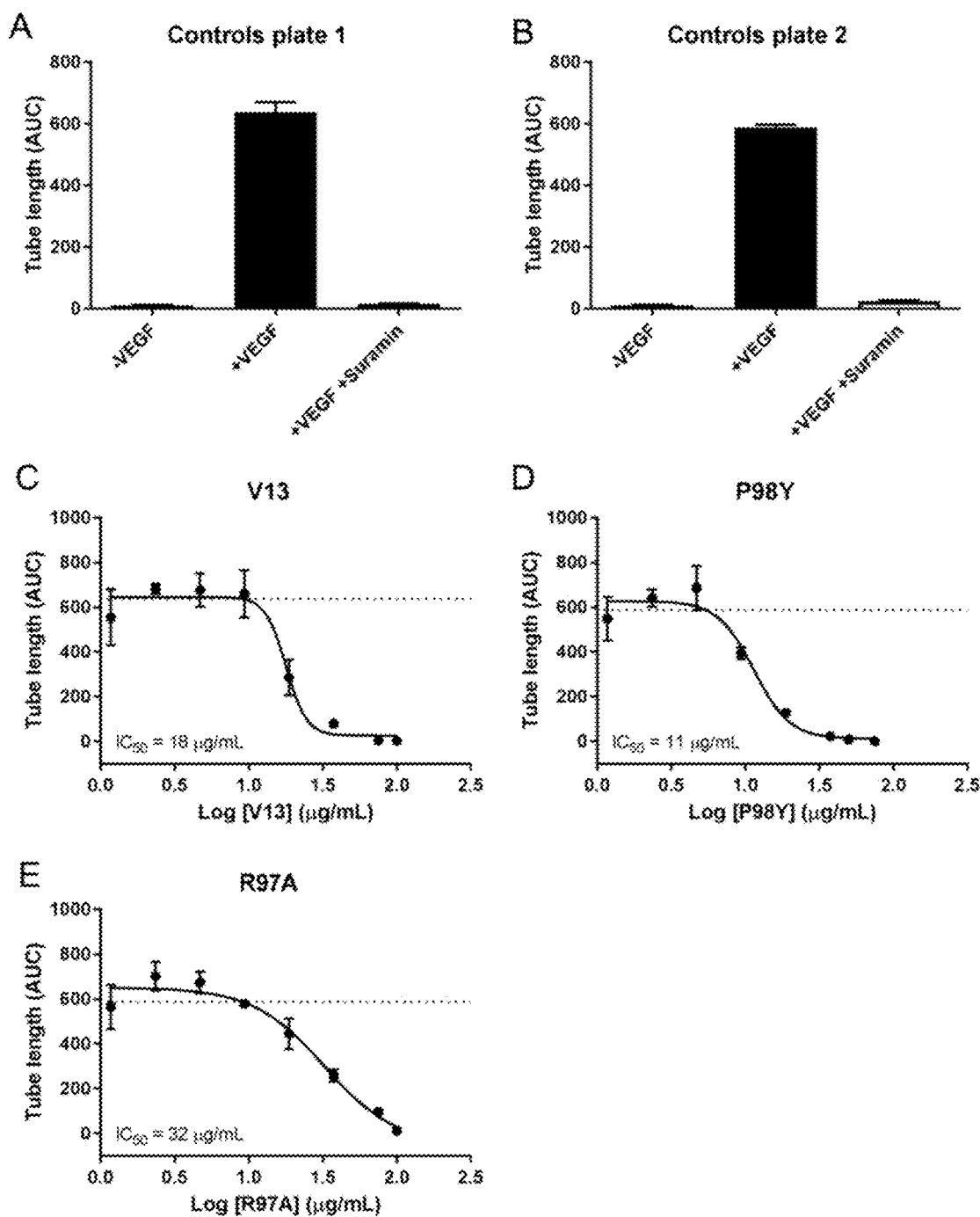

FIG. 4 shows the analysis of the area under the curve (AUC) of the length of the tube as a function of the activity of the different vNARs. AUC values were calculated for the 48-240 hour time points for the tube length using GraphPad Prism. The lines are representative of the average of 8 wells (without VNAR). The curve adjustment (C-E graphs) was performed by nonlinear regression (4 parameters) with GraphPad Prism, and the average of the +VEGF controls is indicated by a dashed line. The data are the average of 8 (A-B) or 3 (C-E) wells±SEM.

Figure 5:
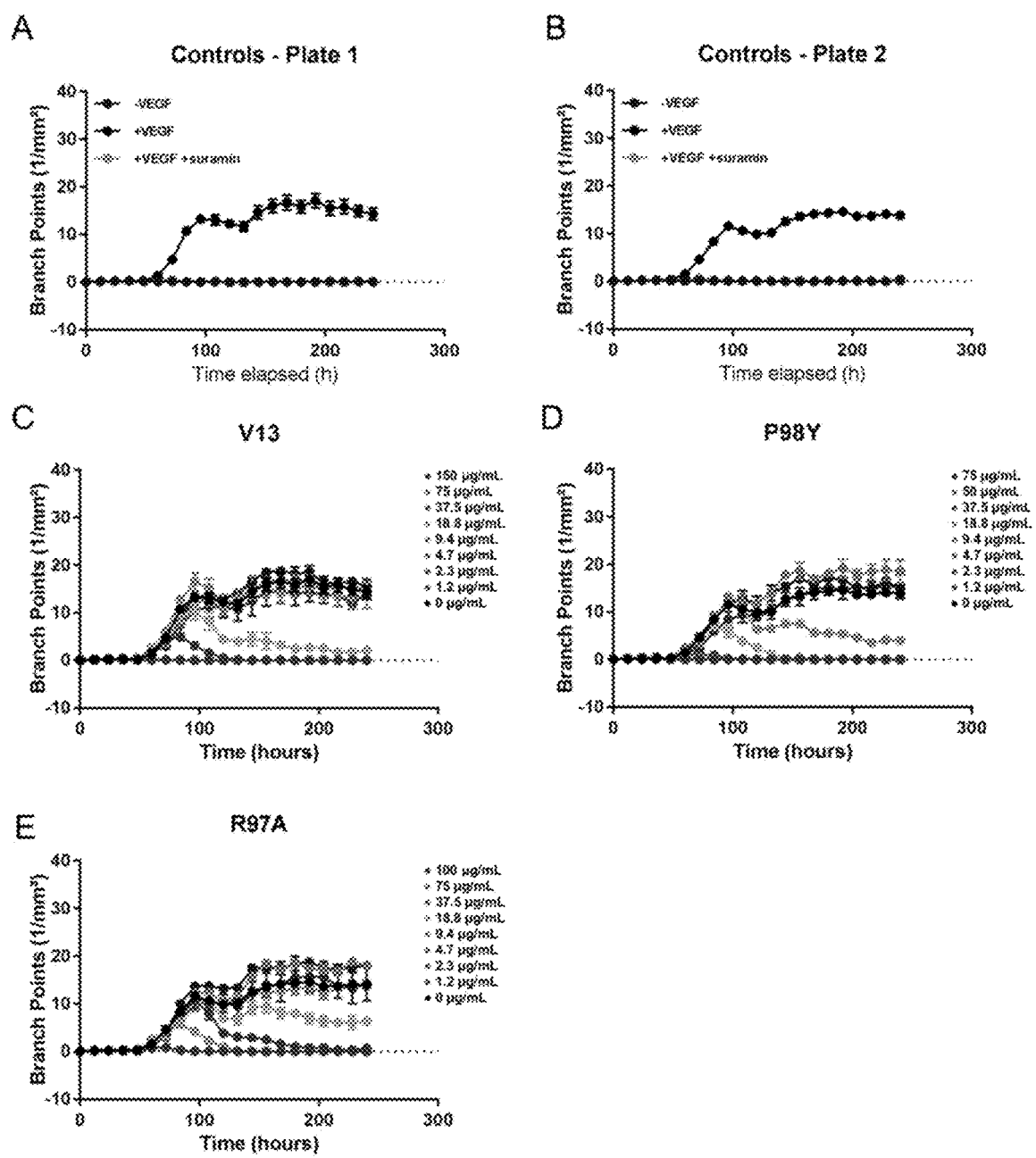

FIG. 5 illustrates the effects of test vNARs on branch points of the network. (A and B) forty-eight hours after seeding: untreated cells (−VEGF); treatment with 4 ng/ml of VEGF (+VEGF) and; treatment with 4 ng/ml of VEGF and 100 µM of suramin (+VEGF+suramin). Network branching was quantified for 240 hours; data is expressed as the average of 8 wells±SEM. (C-E) forty-eight hours after seeding, the cells were treated with 4 ng/ml of VEGF and the indicated concentrations of each test vNAR. Network branching was quantified for 240 hours; data expressed as the average of 8 wells (without vNAR) or 3 wells with the indicated concentrations of vNAR±SEM.

Figure 6:
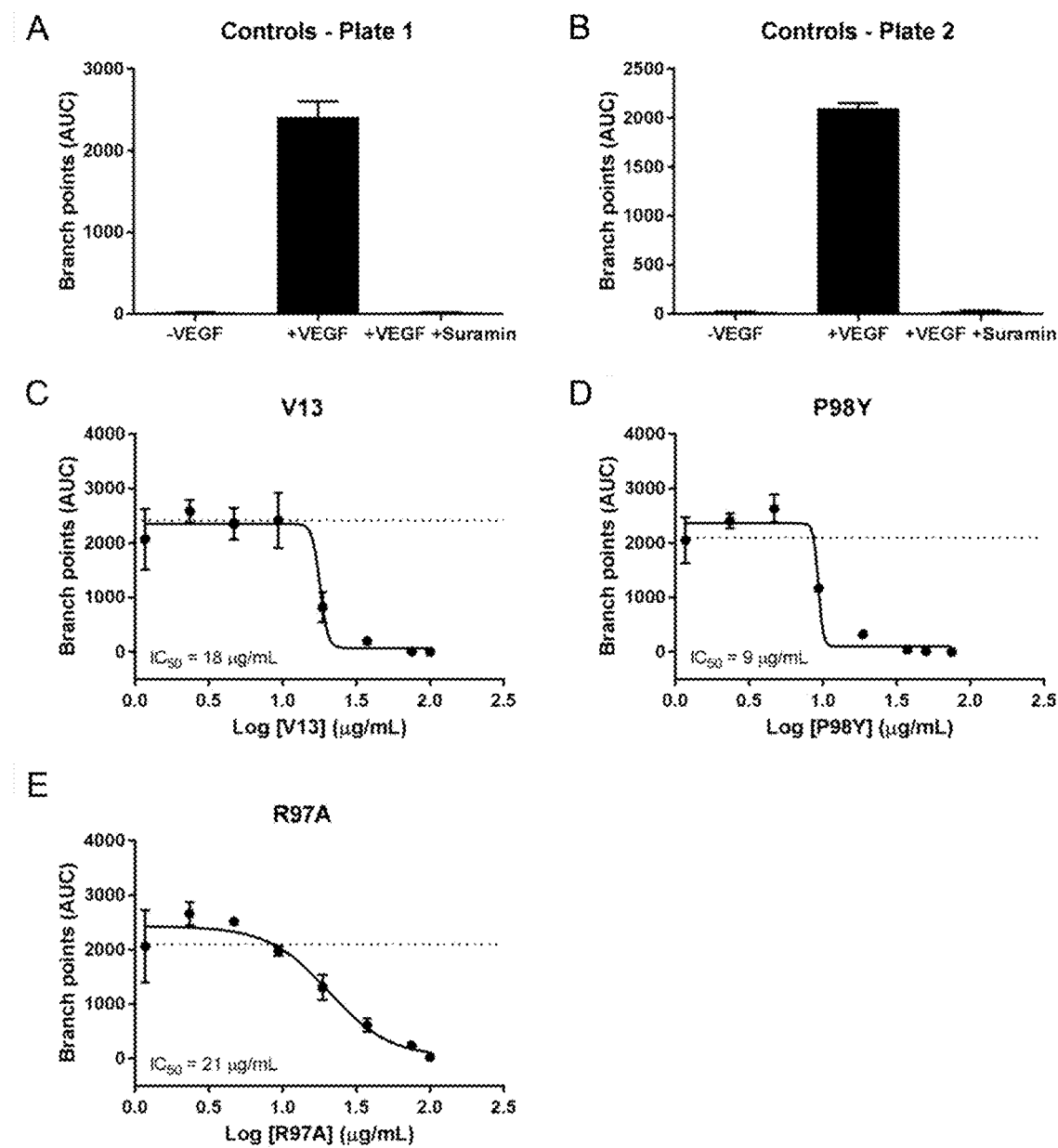

FIG. 6 shows the analysis of the area under the curve (AUC) generated by the vNARs used and the branching generated. The AUC values were calculated for the time points between 48-240 hours for the branch points using GraphPad Prism. The curve adjustment (C-E) was performed by non-linear regression (4 parameters) with GraphPad Prism; the averages of the controls+VEGF is indicated by a dotted line. Data shown as the average of 8 (A-B) or 3 (C-E) wells±SEM.

Figure 7:
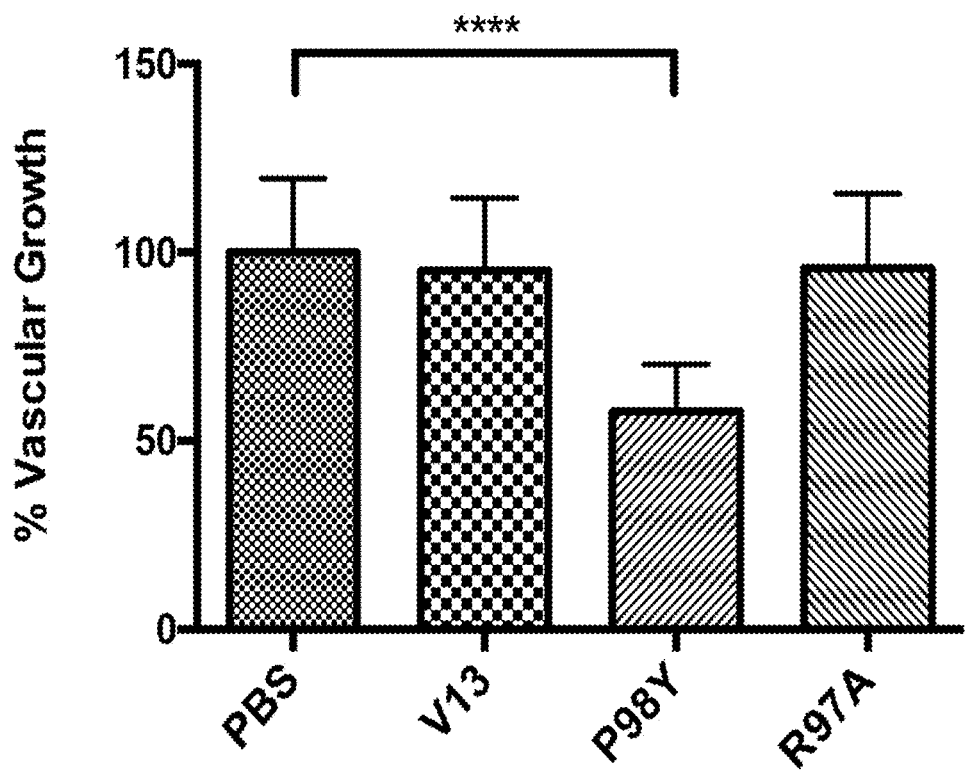

FIG. 7 illustrates the anti-VEGF activity shown by the different vNARs in the inhibition of vascular growth in an in vivo model, using nude mice with tumor implantation. Inhibited angiogenesis is the surrounding of the implanted tumor.

DETAILED DESCRIPTION OF THE INVENTION

The present invention relates to a novel vNAR with anti-angiogenic activity capable of controlling and/or eradicating pathologies associated with overexpression of VEGF in carnivorous animals, particularly neoplastic pathologies on companion animals, such as dogs or cats. This domain is highly related to the endothelial growth factor (VEGF) of carnivores, so it can be used for the treatment of solid neoplastic pathologies associated with high neovascularization.

The vNAR protein sequence of the present invention is identified in the sequence listing as SEQ ID NO:1 and in addition to being presented below, is provided in the ASCII text file entitled, "SequenceListingUS2019P1032CICESE.txt", created on Feb. 19, 2021 and having a file size 4115 bytes which is hereby incorporated by reference in its entirety.

This sequence can be used to actively block the VEGF of mammals of the order of carnivores and is particularly effective in the treatment of cancer associated with neovascularization in the *Canis* and *Felis* genera. Particularly, in the case of dogs, the high incidence of solid neoplasms such as lymphomas, appendicular osteosarcoma, urinary bladder cancer, histiocytic sarcoma, lung cancer, skin cancer, breast cancer, cancerous head and neck tumors, testicular cancer and Thyroid tumors are particularly susceptible to being treated with SEQ ID NO:1 of the present invention, since in all of them an accelerated angiogenesis phenomenon is actively verified, which can be effectively treated with the sequence target of the present invention.

The sequence object of the present invention has been shown to have greater activity and efficacy in the inhibition of VEGF cytokine in the sampled models compared to other VEGF inhibitor vNAR molecules.

Likewise, the present invention relates to an immunotherapy using SEQ ID NO:1 and to pharmaceutical compositions containing effective amounts of the vNAR protein of SEQ ID NO:1 for use in the treatment of solid malignant neoplasms, whose proliferation is strongly linked to overexpression of VEGF in the affected tissues.

The pharmaceutical compositions in which SEQ ID NO:1 of the present invention can be used are non-limiting: injectable solutions, dermal ointments, micro and nanoparticles, liposomes, and biodegradable polymeric matrices.

Example 1. Selection of vNAR Sequences by in Silico Analysis and Inhibition of VEGF In Vitro Four in silico mutants were selected, each with a single mutation in the CDR3 region from a parental sequence. Two increased VEGF recognition and 2 decreased VEGF binding. A fifth clone was designed, in which the 2 mutations were combined with positive effects on the recognition of VEGF. Table 1 lists the mutations of these clones.

```
                                                  SEQ ID No: 1
Ala Ser Leu Asp Gln Thr Pro Arg Thr Ala Thr Arg Glu Thr Gly
                5               10              15

Glu Ser Leu Ser Ile Asn Cys Val Leu Thr Asp Thr Ser His Ile
                20              25              30

Leu Phe Gly Thr Lys Trp Leu Trp Asn Asn Pro Gly Ser Thr Asp
                35              40              45

Trp Glu Ser Ile Thr Ile Gly Gly Arg Tyr Ala Glu Ser Val Asn
                50              55              60

Asn Gln Ala Lys Ser Phe Ser Leu Gln Ile Lys Asp Leu Thr Val
                65              70              75

Glu Asp Ser Gly Thr Tyr Tyr Cys Lys Ala Gln Thr Ile Gly Arg
                80              85              90

Arg Lys Asn Leu Leu Pro Arg Tyr Leu Val Asn Gly Ile Ala Ala
                95              100             105

Met Gly Tyr Ser Ser Ser Asp Tyr Asp Gly Ala Gly Thr Val Leu
                110             115             120

Thr Val Asn
        123
```

TABLE 1

In silico mutations of the parental CDR3

| Clone | Mutation | Effect |
|---|---|---|
| M1 | P98Y | Positive |
| M2 | L99K | Positive |
| M3 | R90A | Negative |
| M4 | R97A | Negative |
| M5 | P98Y + L99K | Positive | vNAR Expression

From the selected sequences, only two were used to carry out the tests; P98Y corresponding to SEQ ID NO:1 and R97A. The genes for the two new vNARs were synthesized by IDT Inc. and subcloned into the vector pET-28a(+) (Novagen). The two resulting clones (P98Y and R97A) and the parenteral sequence (V13) were expressed in E. coli BL21 (DE3) cells (Invitrogen Life Technologies). FIG. 1 shows the analysis of the expressed proteins.

ELISA Test Recognition

ELISA plates were coated with the same amount of VEGF165; then, the wells were blocked with 3% BSA, several dilutions of clones P98Y and R97A, and the parental sequence (V13) were added. FIG. 2 indicates that clone M1 (P98Y) had a greater recognition of VEGF than the parental.

Angiogenesis Assay

In the vascular tube formation assay, a co-culture system of human umbilical vein endothelial cells (HUVEC) expressing GFP and normal human dermal fibroblasts (NHDF) was used. For cell seeding on day 0, one cryogenic vial of NHDF cells was thawed and resuspended in 12 ml of complete seeding medium. Then, 100 µl of this solution was added per well of a 96-well plate. The cells were incubated at room temperature for 1 hour. Then, 1 cryogenic vial of HUVECs was thawed and resuspended in 12 ml of complete seeding medium. HUVEC (100 µL per well) were seeded into the same plate as NHDFs. The cells were incubated at room temperature for another hour. The plate was then examined in an IncuCyte ZOOM and scanned using the "FOIL" scan type. After 24 hours, the culture medium was replaced with 150 µl of growth medium.

Forty-eight hours after seeding, the cells were treated with VEGF at 4 ng/ml and the test compounds at eight concentrations. The results are shown in Table 2.

TABLE 2

Final assay concentrations (FACs) of individual vNARs (µg/mL)

| vNAR | Compound and buffer titrations | | | | | | | | |
|---|---|---|---|---|---|---|---|---|---|
| V13 | 100 | 75.0 | 37.5 | 18.8 | 9.4 | 4.7 | 2.3 | 1.2 | Compound FAC (µg/mL) |
| R97A | 100 | 75.0 | 37.5 | 18.8 | 9.4 | 4.7 | 2.3 | 1.2 | Compound FAC (µg/mL) |
| P98Y | 75 | 50.0 | 37.5 | 18.8 | 9.4 | 4.7 | 2.3 | 1.2 | Compound FAC (µg/mL) |

Serial dilutions of the compounds were prepared using assay media containing VEGF up to the final concentrations in FIG. 3. Then, 150 µl of medium containing the vNARs were added. In untreated wells, media without VEGF were added. For wells without compound, media with VEGF were added. As a positive control, 100 µM suramin was added to the medium containing VEGF. Assay media, VEGF and test vNAR were added to the cells on days 2, 5, 7, 9 and 11.

The formation of vessel tubes by fluorescently-labeled HUVECs was measured using live-cell imaging, and the effects of the vNARs on this process were assessed. The inhibition of vascular tube formation by the vNARs, is shown in FIG. 3. Area under the curve (AUC) values are shown in FIG. 4.

VEGF also increased tube branching, an effect that was inhibited by the suramin positive control, a VEGF receptor inhibitor. All test vNARs decreased tube length and dose-dependent network branching. P98Y and V13 were especially potent inhibitors of angiogenesis (FIG. 5). The AUC values are shown in FIG. 6. Table 3 summarizes the concentrations that were required to inhibit the proliferation of network tube length and network branching.

TABLE 3

Comparison of $IC_{50}$ values from angiogenesis assays

| Clone | $IC_{50}$ angiogenesis: tube length (µg/mL) | $IC_{50}$ angiogenesis: network branching (µg/mL) |
|---|---|---|
| V13 | 18 | 18 |
| R97A | 21 | 33 |
| P98Y | 9 | 11 |

Example 2. VEGF Inhibition In Vivo

In vivo tests were conducted at AntiCancer, Inc. (San Diego, Calif., USA) in accordance with its protocols for handling animals approved under Assurance #A3873-1, and also approved by the Bioethics Committee of the Center for Scientific Research and Higher Education of Ensenada, Baja California (CICESE), approval number 2014/03. In order to minimize the suffering of the animals, anesthesia and analgesics were used for all surgical experiments. Animals were anesthetized by subcutaneous injection of a solution of 0.02 ml of ketamine 20 mg/kg, 15.1 mg/kg xylazine, and 0.48 mg/kg of acepromazine maleate. Animals responses during surgery were monitored to ensure adequate depth of anesthesia. The animals were observed daily and humanely sacrificed through $CO_2$ inhalation when they met the following endpoint criteria: severe tumor burden (more than 20 mm in diameter), prostration, significant body weight loss, difficulty breathing, rotational motion, and body temperature drop. Animals were housed in a barrier facility, on a high-efficiency particulate arrestance-filtered rack under standard conditions of light/dark cycles of 12 hours. Animals were fed an autoclaved laboratory rodent diet. Eight nestin-driven GFP (ND-GFP) mice were used [Amoh Y, Yang M, Li L, Reynoso J, Bouvet M, Moossa A R, Katsuoka K, Hoffman R M. Nestin-driven green fluorescent protein transgenic nude mouse for imaging human tumor angiogenesis. Cancer Res. 2005; 65: 5352-5357], individuals from 6 to 10 weeks old were used per group. ND-GFP mice expressed GFP in nascent blood vessels. Murine Lewis lung cancer cell lines, stably transfected with red fluorescent protein (RFP) were used for implantation of foot cancer cells in the plantar pad ($5 \times 10^5$ cells in 25 µl). The treatment began 3 days after implantation of cancer cells. All vNARs were administered intraperitoneally (i.p.) twice per week for a total of 6 doses over 18 days; each administration contained 27 μg of VNAR in 180 μl of PBS. After day 18, the implanted footpad of the mice in each group was imaged for GFP-expressing blood vessels. The vessel density was calculated as the total length of the blood vessels divided by the observed area. Each individual tumor was collected and, the weighed (g).

Treatment with the P98Y mutant for 18 days and six doses in total, produced a reduced capillary growth around the tumor, showing a significant difference with the untreated controls (P<0.0001, by ANOVA). Inhibition in the case of mutant R97A was comparable with parental v13 VNAR. FIG. 7 shows the percent inhibition of each vNAR. Likewise, V13, P98Y, and R97A were tested to determine their ability to inhibit tumor growth in vivo in the aforementioned mouse tumor model. After day 18, each tumor was dissected, and the weight (g) was measured. Table 4 shows the average normalized weight (n=8) of each treated group, where PBS (untreated mice) represents the maximum recorded weight (100%). Only P98Y shows a statistically significant reduction of the tumor (p=0.02). V13 also shows a reduction in tumor weight; However, it is not statistically relevant.

TABLE 4

Comparison of normalized tumor weight among treatments

| Clone | Normalized tumor weight | Standard deviation | p value |
|---|---|---|---|
| PBS | 1.0 | 0.23 | |
| V13 | 0.63 | 0.31 | 0.06 |
| R97A | 0.76 | 0.24 | 0.16 |
| P98Y | 0.71 | 0.36 | 0.02 |

The assay described above showed without a doubt that SEQ ID NO:1 allows reducing the size of the tumor masses induced in the murine model, which is perfectly extrapolated to dogs or cats, since the murine VEGF sequence SEQ ID NO:2 and, those of cat SEQ ID NO:3 and dog SEQ ID NO:4, are particularly similar. In this regard, it is important to highlight that the VEGF sequences in dogs and cats have a homology of 93.4% with respect to the mouse VEGF sequence, changing only 6 amino acids in the internal region of the protein, as shown in the next amino acid pairing.

```
Mouse VEGF                                              (SEQ ID NO: 2)
Gln Lys Ser His Glu Val Ile Lys Phe Met Asp Val Tyr Gln Arg Ser
1               5                   10                  15
Tyr Cys Arg Pro Ile Glu Thr Leu Val Asp Ile Phe Gln Glu Tyr Pro
                20                  25                  30
Asp Glu Ile Glu Tyr Ile Phe Lys Pro Ser Cys Val Pro Leu Met Arg
            35                  40                  45
Cys Ala Gly Cys Cys Asn Asp Glu Ala Leu Glu Cys Val Pro Thr Ser
        50                  55                  60
Glu Ser Asn Ile Thr Met Gln Ile Met Arg Ile Lys Pro His Gln Ser
65                  70                  75                  80
Gln His Ile Gly Glu Met Ser Phe Leu Gln
                85                  90

Cat VEGF                                                (SEQ ID NO: 3)
His Glu Val Val Lys Phe Met Asp Val Tyr Gln Arg Ser Tyr Cys Arg
1               5                   10                  15
Pro Ile Glu Thr Leu Val Asp Ile Phe Gln Glu Tyr Pro Asp Glu Ile
                20                  25                  30
Glu Tyr Ile Phe Lys Pro Ser Cys Val Pro Leu Met Arg Cys Gly Gly
            35                  40                  45
Cys Cys Asn Asp Glu Gly Leu Glu Cys Val Pro Thr Glu Glu Phe Asn
        50                  55                  60
Ile Thr Met Gln Ile Met Arg Ile Lys Pro His Gln Gly Gln His Ile
65                  70                  75                  80
Gly Glu Met Ser Phe Leu Gln His Ser Lys Cys Glu Cys Arg Pro Lys
                85                  90                  95
Lys Asp

Dog VEGF                                                (SEQ ID NO: 4)
Gly Gly Glu His Lys Pro His Glu Val Val Lys Phe Met Asp Val Tyr
1               5                   10                  15
Gln Arg Ser Tyr Cys Arg Pro Ile Glu Thr Leu Val Asp Ile Phe Gln
                20                  25                  30
Glu Tyr Pro Asp Glu Ile Glu Tyr Ile Phe Lys Pro Ser Cys Val Pro
            35                  40                  45
Leu Met Arg Cys Gly Gly Cys Cys Asn Asp Glu Gly Leu Glu Cys Val
        50                  55                  60
Pro Thr Glu Glu Phe Asn Ile Thr Met Gln Ile Met Arg Ile Lys Pro
65                  70                  75                  80
His Gln Gly Gln His Ile Gly Glu Met Ser Phe Leu Gln His Ser Lys
                85                  90                  95
Cys Glu Cys Arg Pro Lys Lys Asp
```

The present invention has been described according to a preferred embodiment; however, it will be apparent to a technician with average knowledge in the field, that modifications may be made to the invention, without departing from its spirit and scope.

What is claimed is:

1. An anti VEGF vNAR antibody comprising the amino acid sequence of SEQ ID NO: 1.

2. A composition comprising the anti VEGF vNAR antibody of claim 1 and at least one pharmaceutically acceptable excipient.

\* \* \* \* \*

```
                              SEQUENCE LISTING

<160> NUMBER OF SEQ ID NOS: 4

<210> SEQ ID NO 1
<211> LENGTH: 123
<212> TYPE: PRT
<213> ORGANISM: ARTIFICIAL SEQUENCE
<220> FEATURE:
<223> OTHER INFORMATION: Artificial sequence against VEGF, with single
      mutation in the CDR3 region from a parenteral vNAR sequence.

<400> SEQUENCE: 1

Ala Ser Leu Asp Gln Thr Pro Arg Thr Ala Thr Arg Glu Thr Gly Glu
1               5                   10                  15

Ser Leu Ser Ile Asn Cys Val Leu Thr Asp Thr Ser His Ile Leu Phe
                20                  25                  30

Gly Thr Lys Trp Leu Trp Asn Asn Pro Gly Ser Thr Asp Trp Glu Ser
            35                  40                  45

Ile Thr Ile Gly Gly Arg Tyr Ala Glu Ser Val Asn Asn Gln Ala Lys
        50                  55                  60

Ser Phe Ser Leu Gln Ile Lys Asp Leu Thr Val Glu Asp Ser Gly Thr
65                  70                  75                  80

Tyr Tyr Cys Lys Ala Gln Thr Ile Gly Arg Arg Lys Asn Leu Leu Pro
                85                  90                  95

Arg Tyr Leu Val Asn Gly Ile Ala Ala Met Gly Tyr Ser Ser Ser Asp
                100                 105                 110

Tyr Asp Gly Ala Gly Thr Val Leu Thr Val Asn
            115                 120

<210> SEQ ID NO 2
<211> LENGTH: 90
<212> TYPE: PRT
<213> ORGANISM: Mouse
<220> FEATURE:
<223> OTHER INFORMATION: Mouse VEGF sequence

<400> SEQUENCE: 2

Gln Lys Ser His Glu Val Ile Lys Phe Met Asp Val Tyr Gln Arg Ser
1               5                   10                  15

Tyr Cys Arg Pro Ile Glu Thr Leu Val Asp Ile Phe Gln Glu Tyr Pro
                20                  25                  30

Asp Glu Ile Glu Tyr Ile Phe Lys Pro Ser Cys Val Pro Leu Met Arg
            35                  40                  45

Cys Ala Gly Cys Cys Asn Asp Glu Ala Leu Glu Cys Val Pro Thr Ser
        50                  55                  60

Glu Ser Asn Ile Thr Met Gln Ile Met Arg Ile Lys Pro His Gln Ser
65                  70                  75                  80

Gln His Ile Gly Glu Met Ser Phe Leu Gln
                85                  90

<210> SEQ ID NO 3
<211> LENGTH: 98
<212> TYPE: PRT
<213> ORGANISM: Cat
<220> FEATURE:
<223> OTHER INFORMATION: Cat VEGF sequence
```

```
<400> SEQUENCE: 3

His Glu Val Val Lys Phe Met Asp Val Tyr Gln Arg Ser Tyr Cys Arg
1               5                   10                  15

Pro Ile Glu Thr Leu Val Asp Ile Phe Gln Glu Tyr Pro Asp Glu Ile
            20                  25                  30

Glu Tyr Ile Phe Lys Pro Ser Cys Val Pro Leu Met Arg Cys Gly Gly
            35                  40                  45

Cys Cys Asn Asp Glu Gly Leu Glu Cys Val Pro Thr Glu Glu Phe Asn
        50                  55                  60

Ile Thr Met Gln Ile Met Arg Ile Lys Pro His Gln Gly Gln His Ile
65                  70                  75                  80

Gly Glu Met Ser Phe Leu Gln His Ser Lys Cys Glu Cys Arg Pro Lys
                85                  90                  95

Lys Asp

<210> SEQ ID NO 4
<211> LENGTH: 104
<212> TYPE: PRT
<213> ORGANISM: Dog
<220> FEATURE:
<223> OTHER INFORMATION: Dog VEGF sequence

<400> SEQUENCE: 4

Gly Gly Glu His Lys Pro His Glu Val Val Lys Phe Met Asp Val Tyr
1               5                   10                  15

Gln Arg Ser Tyr Cys Arg Pro Ile Glu Thr Leu Val Asp Ile Phe Gln
            20                  25                  30

Glu Tyr Pro Asp Glu Ile Glu Tyr Ile Phe Lys Pro Ser Cys Val Pro
            35                  40                  45

Leu Met Arg Cys Gly Gly Cys Cys Asn Asp Glu Gly Leu Glu Cys Val
        50                  55                  60

Pro Thr Glu Glu Phe Asn Ile Thr Met Gln Ile Met Arg Ile Lys Pro
65                  70                  75                  80

His Gln Gly Gln His Ile Gly Glu Met Ser Phe Leu Gln His Ser Lys
                85                  90                  95

Cys Glu Cys Arg Pro Lys Lys Asp
            100
```